United States Patent [19]

McLeod

[11] Patent Number: 5,014,719

[45] Date of Patent: May 14, 1991

[54] KNEE LOADING AND TESTING APPARATUS AND METHOD

[76] Inventor: Paul C. McLeod, 4 Echo Point, Little Rock, Ark. 72210

[21] Appl. No.: 805,265

[22] Filed: Dec. 6, 1985

Related U.S. Application Data

[63] Continuation of Ser. No. 576,516, Feb. 2, 1984, abandoned.

[51] Int. Cl.$^5$ .............................................. A61B 5/11
[52] U.S. Cl. .................................... 128/774; 128/782; 73/794
[58] Field of Search ....................... 128/774, 780, 782; 73/794

[56] References Cited

U.S. PATENT DOCUMENTS

| | | | |
|---|---|---|---|
| 4,256,095 | 3/1981 | Graham | 128/376 |
| 4,306,571 | 12/1981 | McLeod, Jr. | 128/782 |

OTHER PUBLICATIONS

Lipke et al., "The Rule of Incompetence of the Anterior Cruciate and Lateral Ligaments in Anterolateral and Anteromedial Instability", The Journal of Bone and Joint Surgery, vol. 63-A, No. 6, Jul. 1981, pp. 954-959.
Markolf et al., "Stiffness and Laxity of the Knee-The Contributions of the Supporting Structures", Journal of Bone and Joint Surgery, vol. 58-A, No. 5, Jul. 1976, pp. 583-593.
Moore et al., "Collateral Ligament Laxity of the Knee", The Journal of Bone and Joint Surgery, vol. 58-A, No. 5, Jul. 1976, pp. 594-598.
Krause et al., "Mechanical Changes in the Knee After Meniscectomy", The Journal of Bone and Joint Surgery, vol. 58-A, No. 5, Jul. 1976, pp. 599-604.
Wang et al., "Rotatory Laxity of the Human Knee Joint,", The Journal of Bone and Joint Surgery, vol. 56-A, No. 1, Jan. 1974, pp. 161-170.

Primary Examiner—Ruth S. Smith
Attorney, Agent, or Firm—Jim Zegeer

[57] ABSTRACT

A knee loading and testing apparatus has tibia and femur bone mounting units, respectively, and a quadricep loading means and unit for automatically manipulating the mounting means to the quadricep loading means to derive data regarding the knee joint. The quadricep is variably controlled to allow variation in the torque and pull and at the same time, both the femur and tibia mountings are independently articulatable, and further, these various loadings may be controlled and recorded by a computer and the response to the joint to various loadings may be recorded for future study and analysis by any computer. Preset limits on the application of the quadricep force and body weight are provided and the operator is provided with a visual and audible signal indicating the overload. The machine also disables the control from further increasing these load functions and while the controls for decreasing this loading remain operable. Either drive may be released for the transverse or coronal plane motions while still measuring the angulation of the tibia in both planes. The knee specimen can be rotated about an axis through the hip and ankle, so that viewing, surgical procedures and x-raying may be performed with the specimen in place thus eliminating removal and/or installation errors from the data. The machine uses the quadricep force applied through patella thereby providing for simulation of abnormal patello-femural interaction by providing a wide range of "Q" angle variations, injuries, diseases, abnormalities associated with this particular surface can be studied.

33 Claims, 13 Drawing Sheets

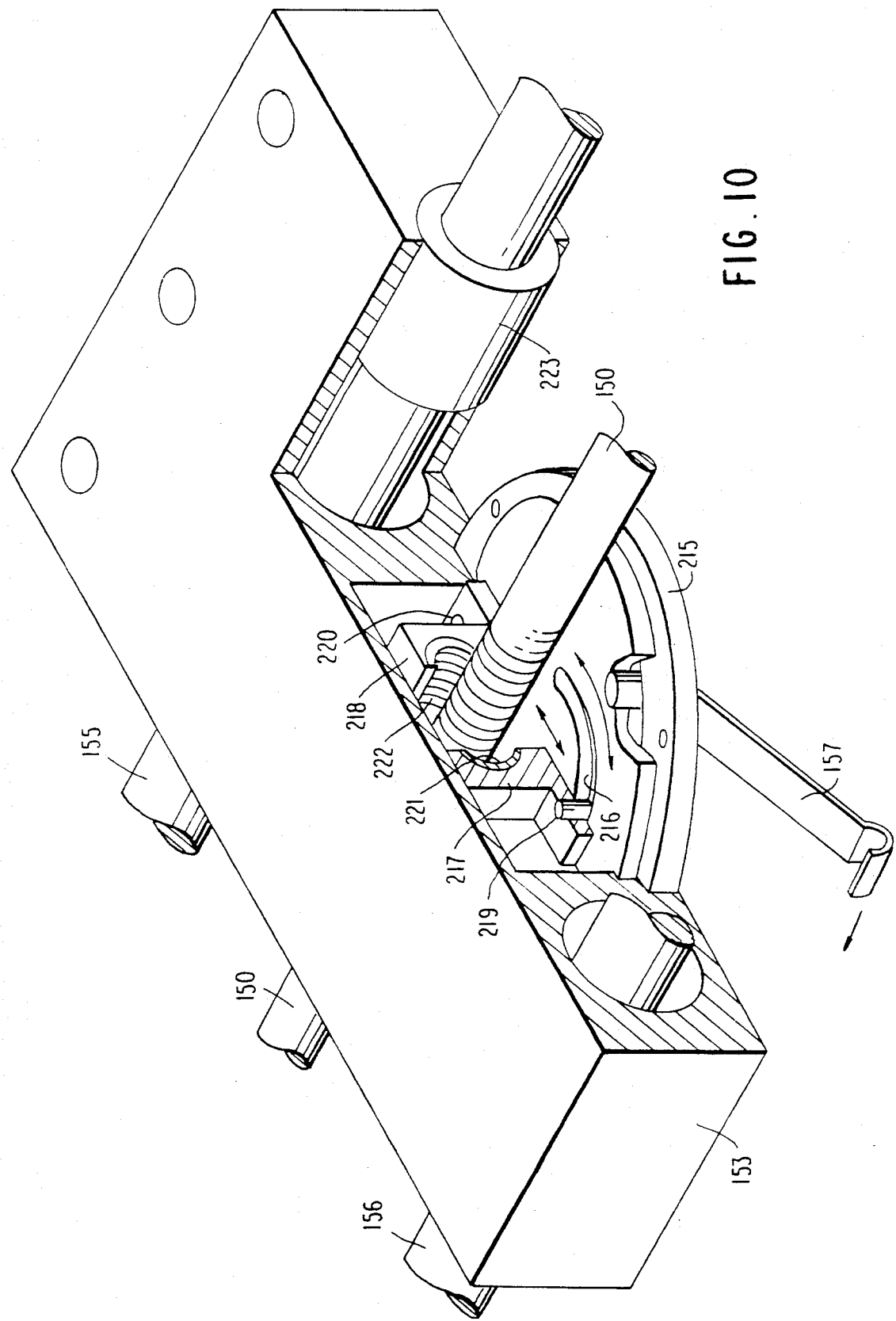

KNEE LOADING AND TESTING APPARATUS AND METHOD

This application is a continuation, now abandoned of application Ser. No. 576,516, filed Feb. 2, 1984.

BACKGROUND AND BRIEF DESCRIPTION OF THE INVENTION

Several devices have been published that measure the anterior-lateral rotational instability of the knee but they are lacking a number of important simulations of the human knee. In a paper entitled "Stiffness and Laxity of the Knee—Contributions of the Supporting Structures" by Markolf et al. which appeared in the July 1976 issue of the Journal of Bone and Joint Surgery, pages 583-604, apparatus for testing various aspects of the knee are disclosed but the data there obtained can be in error because there was no "body weight" or quadriceps force applied so actual knee loading was not reflected in the data. In a paper by Wang et al. entitled "Rotary Laxity of the Human Knee Joint" which also appeared in the Journal of Bone and Joint Surgery", January 1974, page 161-170, a knee apparatus was disclosed which utilized a rotary laxity rig and an automatic. Instron loading machine in which tibial and femural bone fixtures grasp the bone and various rotary and loading forces were applied on the knee joint. Again, there was no actual body weight or quadriceps knee loading. Finally, in an article co-authored by the inventor hereof entitled "The Role of Incompetence of the Anterior Cruciate and Lateral Ligaments in Anterolateral and Anteromedial Instability", by Lipke et al, published in the July 1981 issue of the Journal of Bone and Joint Surgery", pages 954-959, a knee loading and testing apparatus is disclosed wherein a gravity load on the knee is simulated by an air cylinder articulating a mounting for the tibia bone while maintaining stationary the mounting for the femur bone and clamping the quadricep muscle ligament. The fibula bone is left free. That publication is believed to disclose the most pertinent art relative to the present invention.

According to the present invention, the quadricep length is variably controlled to allow variation in the torque and pull and at the same time, both the femur and tibia mountings are independently articulatable, and further, these various loadings may be controlled and recorded by a computer and the response of the joint to various loadings may be recorded for future study and analysis by any computer.

As compared with the disclosures in the above Lipke et al article, the present invention provides for release of both the transverse and coronal plane drives while still measuring angulation. Thus, the present invention provides a releasable drive to the mountings for the femur and tibia so that data may be obtained under a wider variety of simulated loading conditions than heretofore. While the invention has been developed for use in conjunction with cadaver knee joints, it is believed that several modifications of the invention can be applied to live knee joints for in vivos study, particularly of knees having sustained damage as for example an athlete such as a basketball or football player. A closed loop control (servo control) is also provided.

In the device disclosed in the above Lipke et al article, flexion angle is measured two ways, (1) a three plane goniometer as disclosed in my U.S. Pat. No. 4,306,571 is attached to the test fixture or, (2) it is measured at the hip (femur flexion) and the measured value doubled. According to the present invention, the femural flexion and the tibial flexion are independently measured and then they are summed. This is a more accurate way of measurement as it takes into account for differences in the length of the femur and tibia bones.

Only two of nine test variables associated with testing could be measured in the machine disclosed in the Lipke et al article whereas in the present machine, all nine variables can be measured and recorded in nine separate data channels simultaneously. In the machine disclosed in the Lipke et al article, if more than two parameters were required to be compared for a given knee, the knee had to be re-tested, hopefully under the same conditions for each test. In the present invention, one test can provide comparison between any of the parameters in any combination. Hence, the present invention provides a knee testing apparatus which is more accurate and far more flexible than that disclosed in the Lipke article.

In the machine disclosed in the Lipke article, there were no limits as to the magnitude of an input except as determined by the aptitude of the operator. And, with the unknown quality of cadaver knees being tested, the operator could be subjected to serious injury should some component of the knee joint being tested fail. The present invention provides pre-set limits on quadricep force and body weight that can be applied. If either of these are exceeded, the machine provides an acoustic annunciator to advise the operator of an overload, and at the same time, disable the controls which would further increase these load functions. Only the control for decreasing these functions remain operable and the annunciator remains active until the overload is eliminated.

The hip assembly apparatus of the present invention permits the use of attachments for providing "ham string" muscle group simulations without modification of the hip assembly. In addition, the present invention provides measurement of the anterior/posterior force and distance of the tibia with respect to the femur without modification. Furthermore, the present invention provides for locking the hip against rotation in the sagittal plane at any position in its usable range, and, finally, according to the present invention, the vertical motion of the ankle assembly may be locked at any point in the offset range of the ankle.

Advantages of the invention include the following:

the invention provides the knee under test to be stabilized by its own geometry which enhances accuracy of measurement;

has the capability of releasing the drives for either the transverse or coronal plane motions while still measuring the angulation of the tibia in both planes;

has the advantage of releasing both the transvere and coronal plane drives at the same time while still measuring angulation in both planes;

thus, in view of these advantages, the invention can measure in one test, the "screw home" motion of a knee, thus providing a natural test bed for comparisons of "normal" knees and prosthetic implant;

the invention permits anterior/posterior measurement of tibial force and distance with respect to the femur on loaded or unloaded joints;

remote master/slave hydraulic quadricep force mechanisms can easily be connected to hydraulic closed loop control;

all controls are designed to permit simple conversion to closed loop control (servo control) using either the existing computer in the loop or a different one;

since the data is handled by a computer the results of the test may be presented in either English, metric or S1 (Systems International) units as may be desired by the operator;

the data is stored in such manner that the polynominal curve fitting software is included on the control disk (the control software) and can sample and curve fit any pair of data sets of the nine channels stored.

Furthermore, the invention provides accurate testing and teaching of surgical/reconstruction techniques because it permits the knee to be its own standard for before and after surgery on the specimen. Since, in the present invention, the knee specimen can be rotated about an axis through the hip and ankle, viewing, surgical procedures and x-raying may be performed with the specimen in place thus eliminating removal/installation errors from the data. During the data taking sequence, the invention measures and stores all nine data channels in approximately 600 microseconds, thus assuring that there is no significant time change or phase shift from the first to last measurement. Finally, since the machine uses "quad force" applied through the patella and permits simulation of abnormal patello-femural interaction by providing for a wide range (plus or minus 20 degrees) of "Q" angle variation, injuries, diseases and abnormalities associated with this articular surface can be studied (the Q angle is the angle between the direction of quad force pull and the center line of the femural shaft and the medial/lateral direction).

BRIEF DESCRIPTION OF THE DRAWINGS

The above and other objects, advantages and features of the invention will become more apparent in the following specification when considered with the accompanying drawings wherein:

FIG. 10 is an isometric partial sectional view of the ankle assembly drive block.

DETAILED DESCRIPTION OF THE INVENTION

Figure 1:
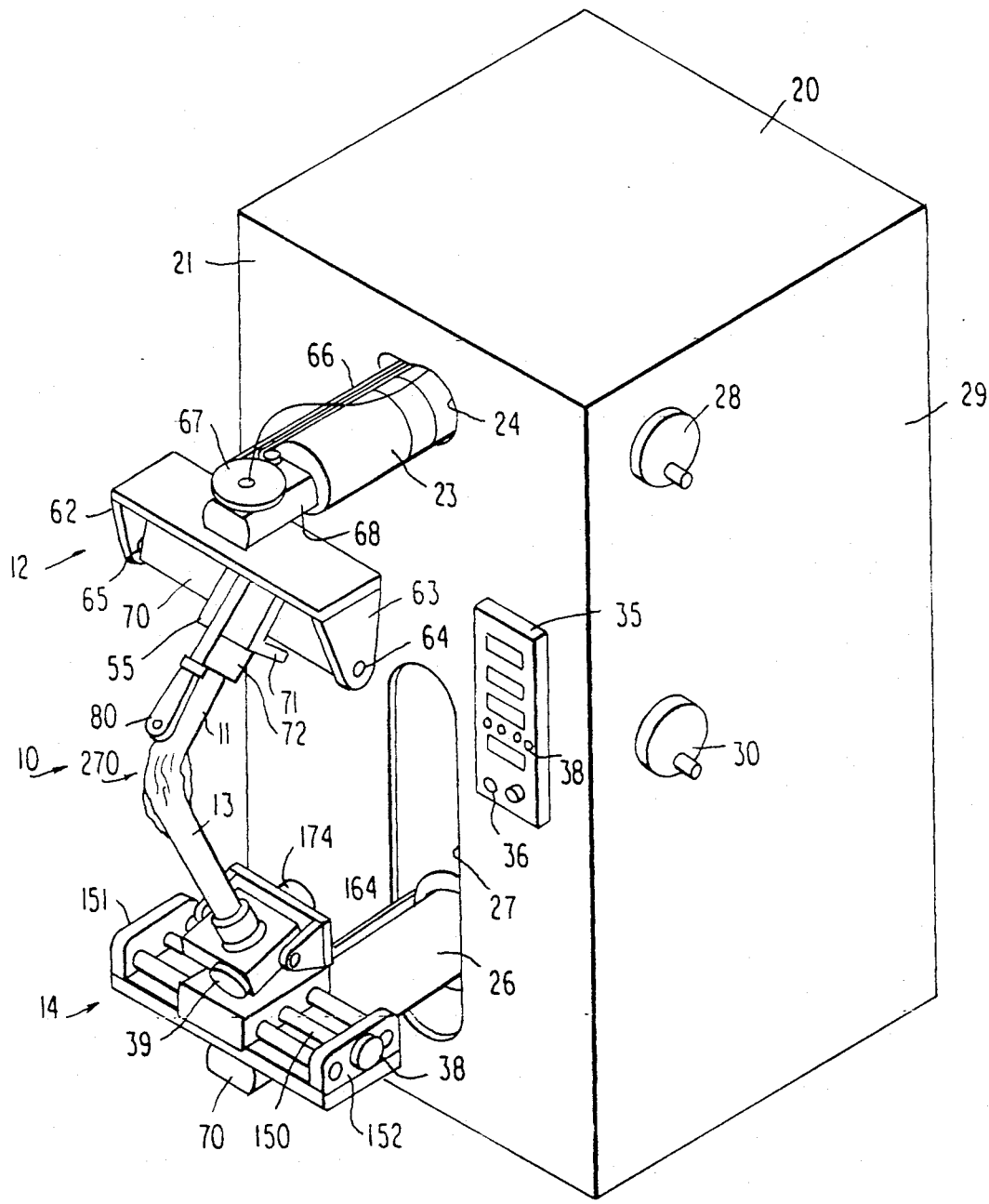
FIG. 1 is an isometric view of a knee loading and testing apparatus incorporating the invention.

Before embarking upon the detailed description, a general testing procedure will be described in connection with the isometric view shown in FIG. 1. During the testing procedure, the cadaver knee 10 is mounted in the assembly; the femur or thigh bone 11 is attached to the hip assembly 12 and is only permitted to move in the forward or sagittal plane. The tibia or shin bone 13 is mounted in ankle assembly 14 and as will be described more fully hereafter, in testing, the ankle assembly is moved in a medial lateral direction, sometimes referred to as the coronal plane or also as the varus/valgus (V/V) angulation. In the terminology used in some of the papers referred to hereinabove, the term "transverse rotation" is used for internal/external rotation of the tibia; the term "varus/valgus angulation" is referred to the coronal plane motion and medial/lateral motion all refer to the same movement. The invention provides all the necessary range of motion and forces to permit complete testing of the knee joint specimen directly from a cadaver specimen or with an implantable prosthetis installed.

Figure 4:
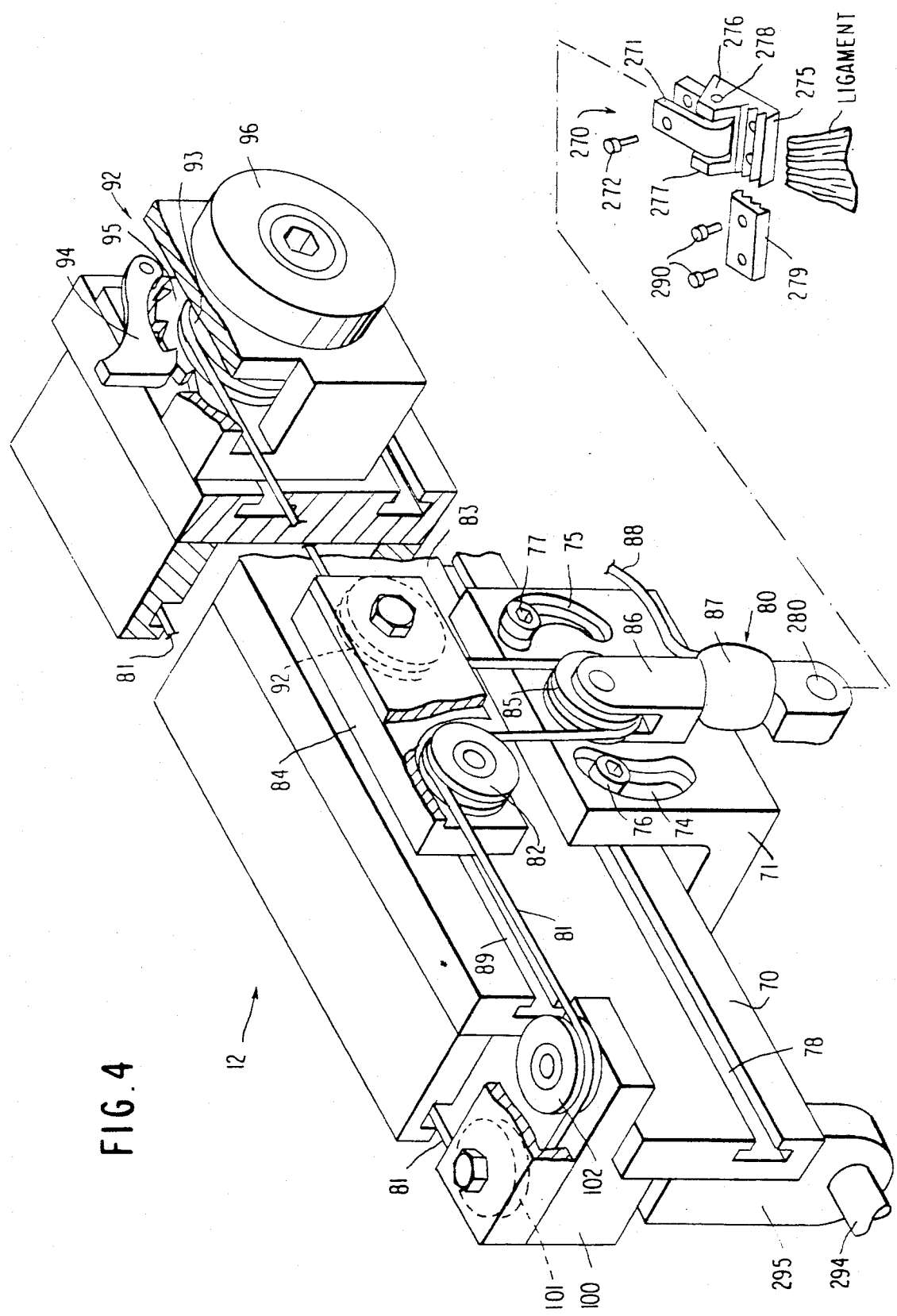
FIG. 4 shows the hip plate assembly.

In the embodiment shown in FIG. 1, a cabinet 20 houses all of the mechanical and most of the electrical components described later herein. Hip assembly 12 protrude from the upper portion of the front panel 21 of cabinet 20. In this embodiment, hip assembly 12 is fixed in a vertical space inasmuch as it does not move up and down or in or out and permits motion of the hip or limits motion of the hip to the sagittal plane during testing. It will be appreciated that one would not go beyond the scope of the invention by providing other movements of the hip assembly 12 in addition to those disclosed herein. While the hip assembly 12 will be described in greater herein in connection with FIG. 4, it will be noted that in FIG. 1, the hip assembly 12 is mounted on an arm 23 which protrudes through opening 24 in front panel 21 of cabinet 20.

Ankle assembly 14 is mounted on an arm 26 which protrudes through slot 27 in front panel 21 which permits the ankle assembly 14 to move up and down in slot 27 for a total distance of approximately 18 inches, 10 inches of which are provided by an electromechanical offset (described later herein) which permits testing of various lengths of specimen without going beyond the range of the body weight motion. The remaining 8 inches of travel is provided by the body weight control system described later herein. Ankle assembly 14 is designed so that it provides the necessary angular motion in the sagittal coronal and transverse planes to perfectly simulate the normal angle. A control crank 28 is provided on the right side panel of cabinet 20 which control 28, as will be described more fully hereinafter, causes the hip assembly 12 and ankle assembly 14 to rotate in synchronism about a vertical axis passing through the center of the hip and ankle assemblies, respectively. This permits testing the knee 10 at any rotational angle about this axis, inspection of the knee from any direction and operating on the knee conveniently from the posterior and interior medial or lateral directions. This motion can be achieved when a simulated full body weight is applied to the knee specimen 10. This is a vertical axis to the hip and ankle assembly which has not heretofore been available and considerably enhances the ability of the surgeon or researcher to completely test the knee specimen and, particularly, to x-ray the knee specimen from any direction under any condition of loading and flexion.

A further control 30 is provided on side panel 29 which causes the knee to flex and extend in the sagittal plane. As will be described more fully hereafter, control 30 operates a hydraulic master cylinder 121 which, in turn, controls a slave hydraulic cylinder 125 located in hip assembly 12 which in turn activates a cable attached to the knee cap which simulates the changing of the length of the quadriceps muscle and causes the knee to flex and extend. Hydraulic control was chosen for this particular application because it can be done remotely and secondly, it provides a safety feature. The remote operation of the quadricep pull to produce flexion extension of the knee is desirable so that the researcher is not required to stand in front of or in close proximity to specimen 10 during the application of the quadricep force during testing. In the event that the quadricep clamp attachment (see FIG. 4) which attaches to the tendon protruding from the knee lets go, the body weight system will cause a rapid rise in the ankle assembly 14 over a short distance which causes the quadricep clamp to swing out and perhaps injure the researcher that may be standing directly in front of the specimen 10. By having the control 30 remote and located on one side of the panel, flexion extension can be controlled remotely with no danger to the operator.

Another reason for selecting a hydraulic system is that once the force has been removed on the master/slave hydraulic system, there is no further action of the cylinder since the master cylinder is screw driven, whereas had it been pneumatic, the slave cylinder would continue to move until the pneumatic pressure had been dissipated against some force.

Operational control for the knee machine is found on display panel 35. Panel 35 has dedicated meters for indicating the quadricep force, body weight, and total knee flexion. These are not, however, data meters but are there for the purposes of setting up the machine and for knowing approximately what values are associated with these particular parameters. A further meter on panel 35 is switchable to the remaining six data parameters of the machine. These are rotational torque, and the subsequent angle which is referred to the transverse plane; varus/valgus angulation angle and necessary force which is referred to the coronal plane; and the anterior/posterior force and tibial angle which is related to the drawer sign test.

The anterior/posterior transducer is used on the anterior/posterior test with the basic machine and is plugged into jack 36 of meter panel 35 when it is desired to make this measurement. Also located on meter panel 35 are four push button switches 38, two of these switches controlling the electromechanical off-set increase which moves the ankle assembly 14 up and decrease which moves the ankle assembly 14 down. The other two switches control the body weight increase which increases the body weight force and decrease which decrease the body weight force. Both of these push buttons which increase the above mentioned functions are automatically disabled in the event the quadricep force exceeds 500 pounds and if the body weight exceed 300 pounds force. The remaining two controls located on ankle assembly 14 are the right end of the control rotation which imposes a varus/valgus force and subsequent angulation and in the front of the rotational force in the angle is control 39 which causes the tibia 13 to rotate.

Figure 2:
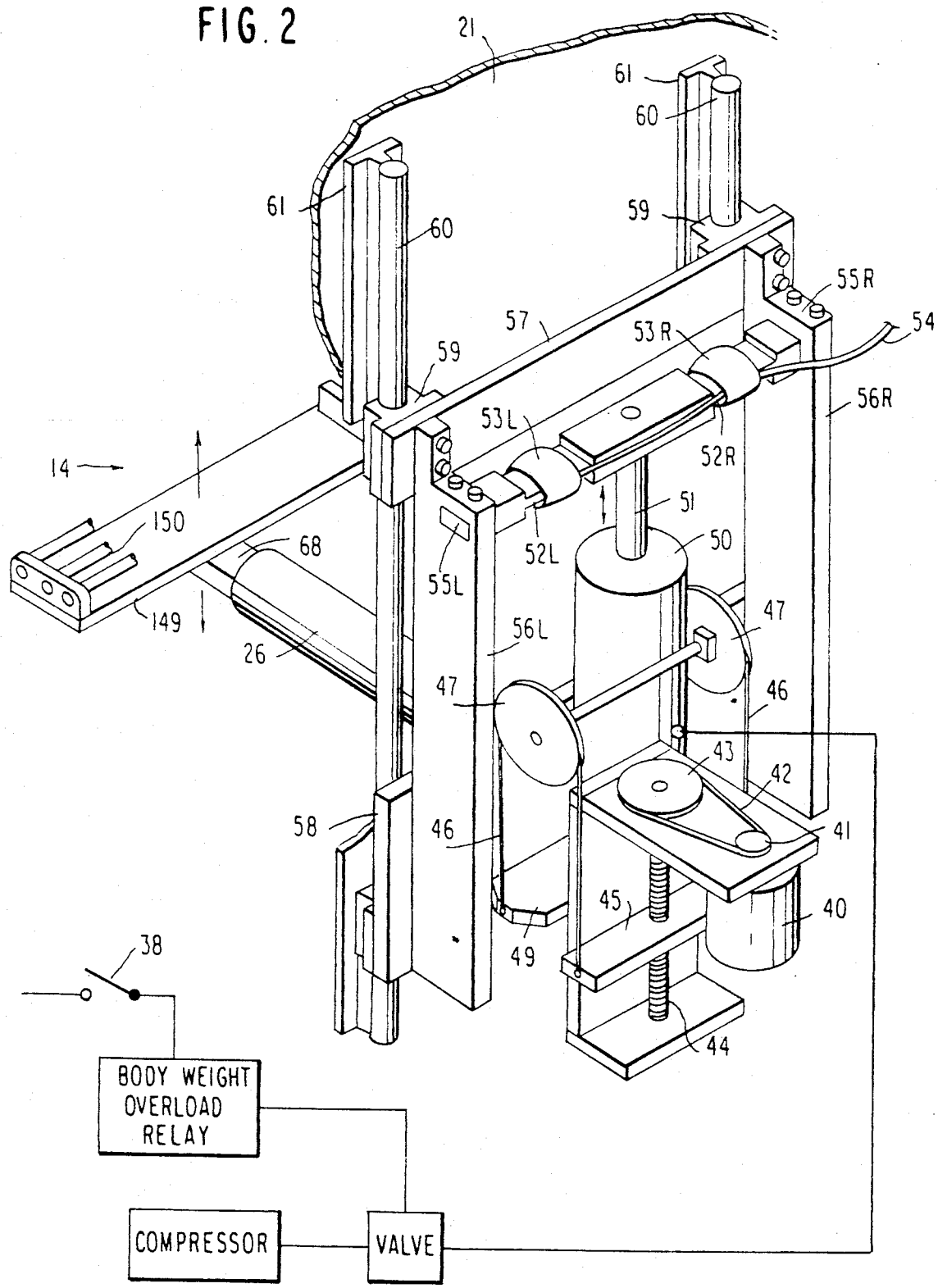
FIG. 2 is an isometric view of the automechanical off-set control motor and drive assembly in the body weight loading system and transducer means.
Figure 12:
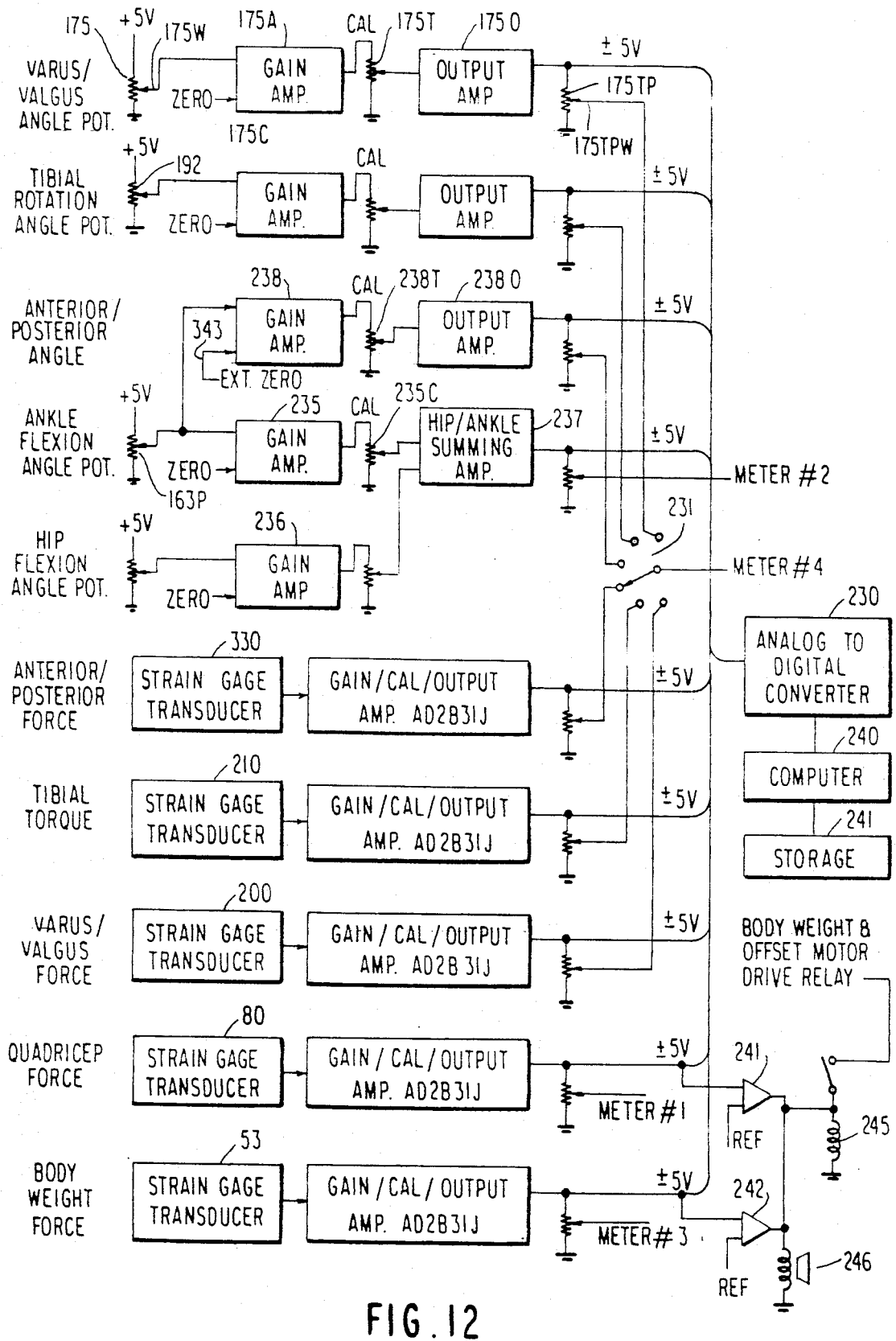
FIG. 12 is a block diagram of the electronic circuitry involved.

FIG. 2 shows the automatic off-set control motor and drive assembly and the body weight system along with the body weight transducer and the devices for allowing these motions to take place with minimal frictional contribution from the overall machine to the recorded data. As shown in FIG. 2, the electromechanical ankle off-set drive assembly or mechanism includes a drive motor 40 having a drive sprocket 41 on the shaft thereof coupled by a drive chain 42 to a driven sprocked 43 which drives drive screw 44 to rotate in the desired direction thus moving drive nut and plate 45 up or down on lead screw 44. Drive nut and plate 45 is a plate which has secured to each end stainless steel aircraft cables 46 which pass over pullies 47 and are then attached to platform 49. Platform 49 supports a pneumatic cylinder 50 which receives air from a supply 50S via a pressure regulator (model 10, motorized, 6 fpm, 120 vac/60 Hz) 50R. Regulator 50R controlled by overload relay 245 (FIG. 12). As lead screw 44 rotates, the nut and drive plate 45 moves up or down causing the cables 46 to be shortened thus raising the pneumatic cylinder 50 as the motor is driven in the desired direction. This causes the entire body weight assembly and ankle assembly 14 to move upward. This permits the adjustment of the offset in the ankle assembly 14 without effecting any of the body weight control motion so that shorter or larger specimens may be accepted. This motion is automatically controlled by the maximum range by limit switches (not shown) to prevent damaging lead screw 44 and nut plate assembly 45.

The simulation of body weight is controlled by pneumatic cylinder 50 and the regulator assembly 50R. The pneumatic regulator 50R is controlled from one of the front panel switches and applies an increasing air pressure from a supply 50S to pneumatic cylinder 50. The piston rod 51 is coupled to the piston (not shown) in cylinder 50 and to a body weight transducer 52 which measures the total force on the ankle assembly 14 along with the total weight of the ankle assembly including everything from the body weight transducer through the ankle assembly itself. Body weight transducer 52 is a precision strain gauge transducer assembly and supplies or transmits a balanced force symmetrically thereby simulating the application of body weight to the knee specimen 10. As noted, the body weight transducer is a precision strain gauge which has a pair of laterally extending transducing arms 52L and 52R both of which are provided with strain gauges 53L and 53R, respectively, and lead wires 54 coupling these transducer outputs to the electronic circuitry described in FIG. 12. The lateral ends 55R and 55L are secured in a pair of vertical frame elements 56L and 56R which are rigidly secured together by a pair of cross braces, upper cross brace 57 and lower cross brace 58, to which are secured linear bearings 59 (the lower bearings secured to cross brace 58 not being visible in this view). There are four linear bearings 59 which ride on a pair of spaced case hardened (60 case) steel shafts 60 securely fastened by rails 61 to the front panel frame plate 21. Hardened steel shafting 60 and linear bearing elements 59 provide a nearly friction free pathway of ankle assembly 14 to move up and down and absorb all of the loads not experienced by the body weight transducers. Those loads were not in the plane of interest and therefore would not be registered on the body weight transducer. Thus, the machine has the advantage of the off set drive which has been discussed above of 10 inches to permit longer and various length specimens to be tested.

It has over twice as much body weight motion and approximately three times as much body weight force available to be applied to the specimen. It should be noted that the stainless steel aircraft cables 46 are applied to support the body weight cylinder in such a manner that the force is directly across the center line of the body weight cylinder and thus imposes no torque or bending moments to the cylinder.

The support arm 26 for ankle assembly 14 is secured to lower cross brace 58 by bolting, welding or the like.

Figure 3:
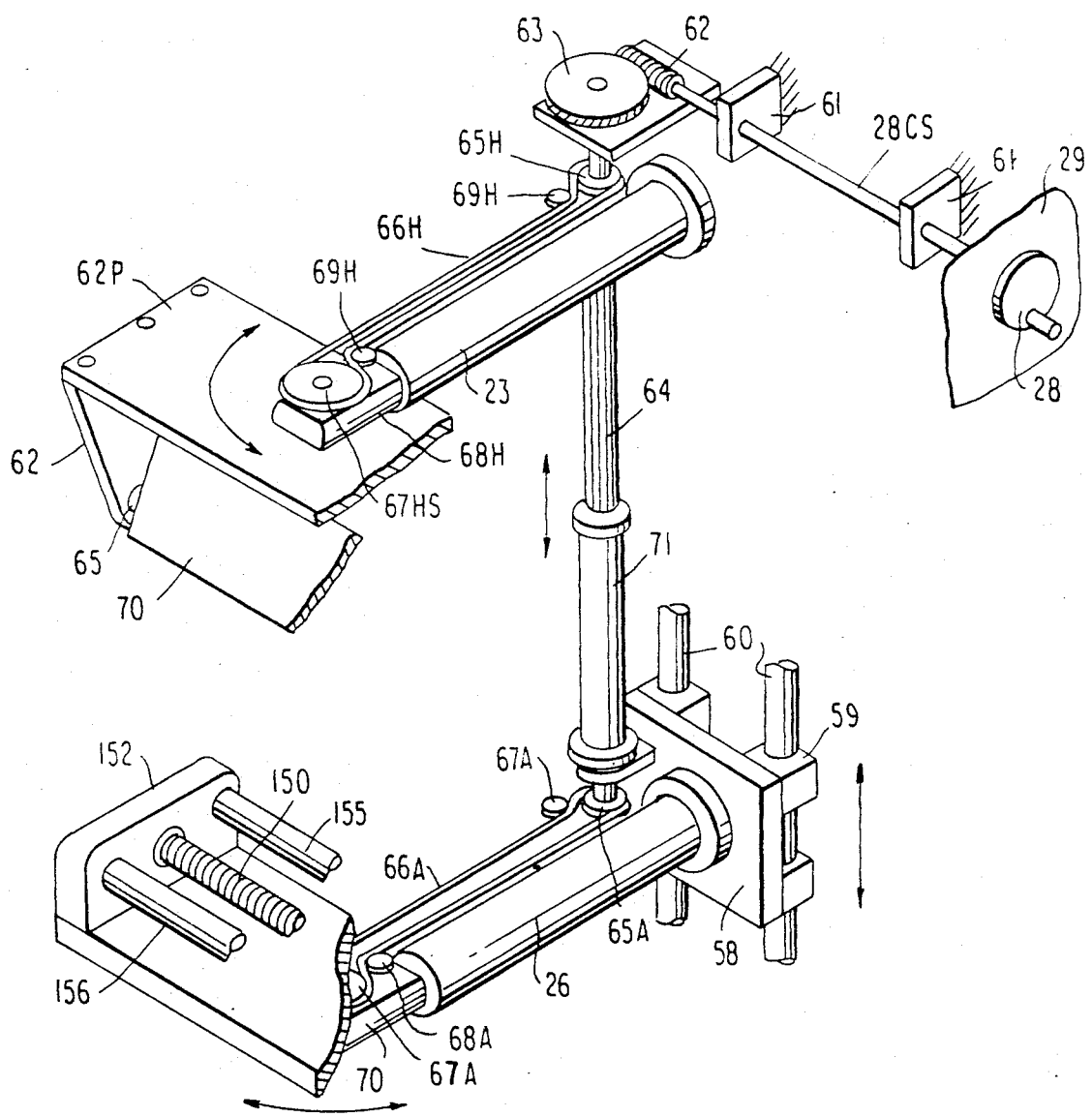
FIG. 3 illustrates the drive for rotating the hip and ankle assembly.

Referring now to FIG. 3, the rotation of hip assembly 12 and ankle assembly 14 about the vertical axis between the center lines thereof is accomplished by rotation of control crank 28. Control crank 28 is secured to one end of control shaft 28CS which is journeled in bearings 61 and control shaft 28CS has a worm gear 62 on the opposite end which is meshed with gear 63 on the upper end of splined shaft 64. A sprocket 65 is secured to upper end of shaft 64 and is coupled by sprocket chain 66 to a hip assembly drive sprocket 67 which is rotatably mounted on the outer flat end 68H of hip assembly support arm 23. A pair of idler sprockets 67H assure tautness in sprocket chain 66 in connection with sprocket 67H and guides the chain around the non-flat end of hip assembly support arm 23. A similar sprocket and chain drive assembly 65a, 66a, 67a, 68a and 69a are provided for rotating the ankle assembly 14 mounted on the outer most end 68A of ankle support arm 26. A lost motion connection is provided between the splined shaft 64 and drive sprocket 65a, which is comprised of a tube 71 for slidably or axially receiving splined shaft 64 therein and coupling rotary motion to sprocket 66A. Thus, the rotation of control 28 causes rotation about the axis of spline assembly 64 which synchronises the motion drive chain sprockets and chains for both the hip and ankle assemblies. This insures that both the hip and ankle assemblies rotate in synchronism when control 28 is rotated. The capability to rotate the hip assembly 12 and ankle assembly about the vertical axis provided by this apparatus is unique and provides a considerable advantage to the surgeon and researcher.

The hip assembly 12 includes a main frame assembly comprising base plate 62P secured to shaft 67HS upon which sprocket drive 67H is secured, shaft 67HS being journeled in portion 68H support arm 23. Two side plates 62, 63 have bearings 64, 65 for receiving short axle stubs 294 extending laterally from bracket 295 (only one shown in FIG. 4 but there being a similar structure on the opposite end). Bracket 295 is secured to hip plate assembly 70. Axles 294 form pivots to permit assembly of the entire assembly only in the sagittal plane. Femural mounting angle 71 is mounted on the bottom portion of hip plate 70 and the femural bone cup 72 (see FIG. 1) attaches to the bottom of femural mounting angle plate 71 by cleats (not shown) and securely attaches the femur bone to the hip plate assembly 70 and hip assembly 12. Femural bone cup 72 is similar to tibial bone cup 170, shown in detail in FIG. 6. The angle plate 71 has a pair of arcuate slots 74, 75 and a pair of securing bolts or cap screws 76, 77, respectively, provide an adjustable attachment means for securing the femural bone cup 72 to hip assembly 12 so that the femur and femural angle may then be set to any angle by cap screws 76 and 77 for setting the proper angle in order for the femur to be properly mounted with respect to the hip plate. Nuts on the ends of cap screws 76 and 77 are fitted into T shaped slot 78 permitting sliding it along to any position in slot 78 before tightening cap screws 76 and 77 respectively. This permits testing of either left or right knee specimens and abnormal and unusual femural angles.

Quadriceps forces is applied to the quadriceps force transducer 80 through cable 81. Cable 81 passes around two pullies 82, 83 carried in quadriceps support bracket pulley block assembly 84 and further through a pulley 85 journaled in a clevis 86 in the upper end of quadricep transducer 80. The signals generated in quadriceps transducer strain gauge 87 are conveyed by wires 88 to the electronic circuit shown in FIG. 12. The quadriceps force pulley block assembly 84 may be adjusted in position at any place along slot 89 in a manner similar to the adjustment of hip angle plate 71 by the adjustment and tightening of cap screws 90 and 91. As shown, a cover plate 92 protects pullies 82 and 83 from bending and permits them to freely rotate. Thus, the pulley block assembly 84 may be positioned to provide abnormal angles for testing for abnormal conditions. Cable 81 continues onto the quadriceps cable storage assembly 92 which stores approximately 15 inches of cable to thereby accomodate the testing of both long and short knee specimens. The cable storage and drum assembly includes a drum 93 with a pawl 94 and ratchet locking assembly 95 and a knurlled handle 96 operated by the operator causes the cable to be wound up on drum 92 and thus stored. The cable is easily retrieved by lifting the pawl 94 from engagment with ratchet 95. A weak spring, (not shown), maintains the pawl in engagment with the ratchet 95. It should be noted that cable 81 is used to support the quadriceps force transducer 80 such that the cable experiences only about one half of the force that the transducer does inasmuch as the cable passes around the pulley 85 at the upper end of quadriceps transducer 80. This limits the tensile force in the cable to about 250 pounds or one half the quadriceps force so that it remains with a safety factor of approximately four. This also means that the cable must move twice as far as the quadriceps transducer 80.

Figure 5:
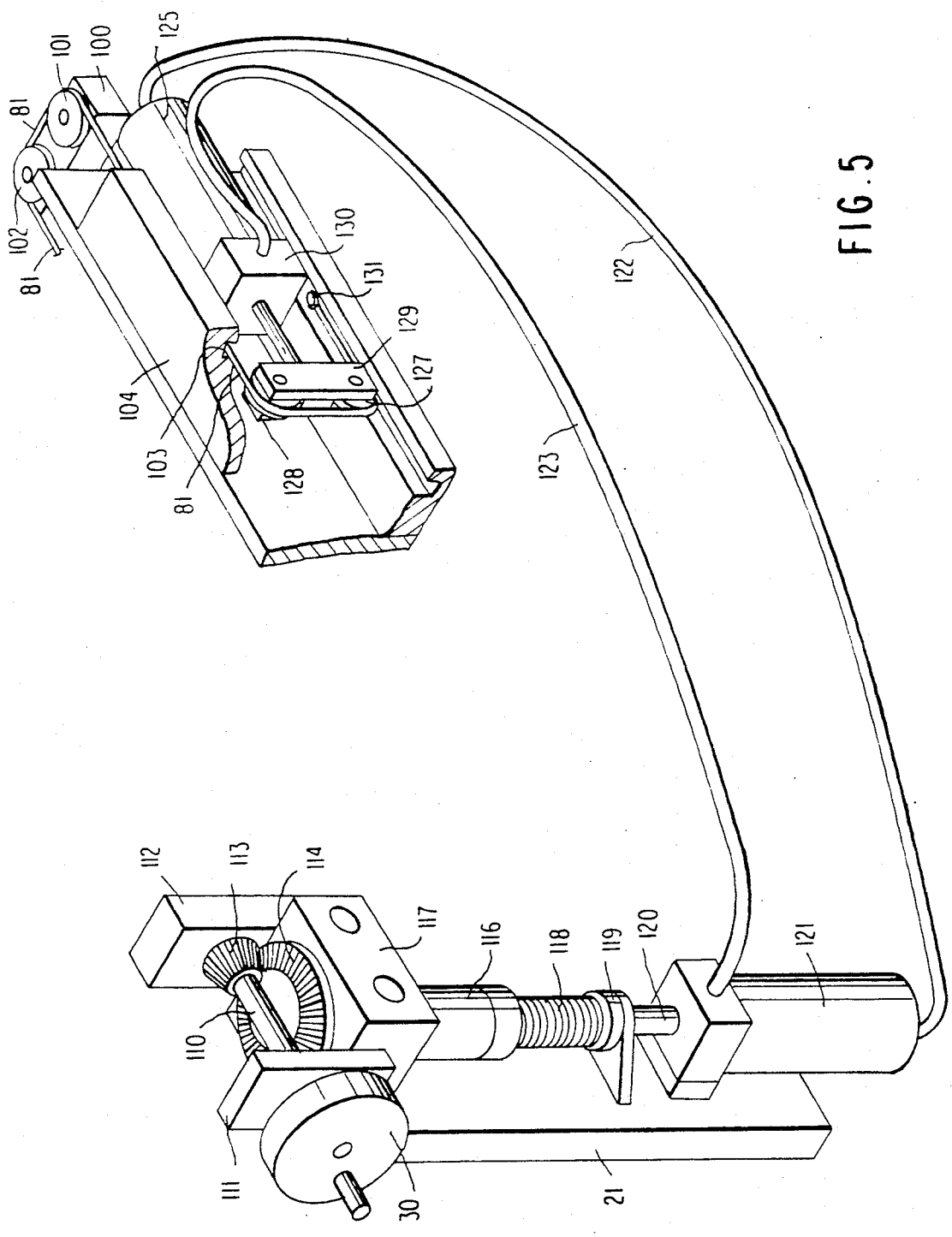
FIG. 5 illustrates the master/slave hydraulic system for applying the quadricep force.

The quadricep clamp 270 includes a U-shaped coupling member 271 which the legs pivotally connected by pin 272 passing through a bore 273 in the lower end of quadricep transducer 80 toothed member 275 has a pair of arms 276 and 277 through which coupling pivot pin 278 passes. A toothed bar member 279 is fastened by screws 290 to toothed member 275, the teeth on toothed member 275 and bar member 279 grabbing the tendon to simulate the quadricep muscle. At the rear end of the hip plate assembly is the quadriceps corner bracket assembly 100 which carries a pair of pullies 101, 102 which pass the quadriceps pull cable 81 through the guide way 103 in plate 104 in the back of hip plate assembly 70, all as shown in FIG. 5. A master/slave hydraulic system for application of the quadriceps force is shown in FIG. 5.

Referring to FIG. 5, control crank 30 drives shaft 110 which is journaled in bearing blocks 111 and 112. Gear 113 on shaft 110 is meshed with gear 114 secured to lead screw nut assembly 116 rotatably mounted in frame block 117 which, in turn, is supported on panel plate 21. Lead screw 118 is engaged with lead screw nut assembly 116. The lower end of lead screw 118 is guided by a bracket 119 to engage piston rod 120 of master hydraulic cylinder 121. Thus, rotation of crank 30 causes the double gear assembly 113, 114 to push the piston coupled to piston rod 120 along the hydraulic cylinder which in turn displaces a metered amount of hydraulic fluid through flexible interconnecting hydraulic lines 122 and 123 and slave hydraulic cylinder 125 on the back side of the hip plate assembly 70. The piston in slave cylinder 125 moves, preferably in exact synchronism with the piston in the master cylinder 121 since they are both identical in nature mechanically. However, the invention encompasses movements other than in exact synchronous. Slave piston rod 126 drive pulley assembly 127 which has a pair of pullies 128 and 129 about which is a trained cable 81, the end of cable 81 being secured to hip plate assembly 70 or to the head 130 of slave cylinder 125 at securement point 131. Thus, the quadriceps pull cable 81 moves twice as fast as pulley assembly 129 with the result being that the quadricep transducer assembly 80 and clamps 270 are displaced or moved exactly the same amount as the piston in the hydraulic slave cylinder 125 which moves the exact same amount as the piston and the hydraulic master cylinder 121. Additionally, the force in the piston rod of the slave cylinder is identical to the force of the quadricep transducer. Also included on the master cylinder assembly is an anti-rotation device 119 at the lower end of lead screw 118 so that no rotational torque is applied to the hydraulic master cylinder shaft 120. Thus, the hydraulic master slave system is a precision system and it does permit flexion extension to be controlled very carefully.

Figure 6:
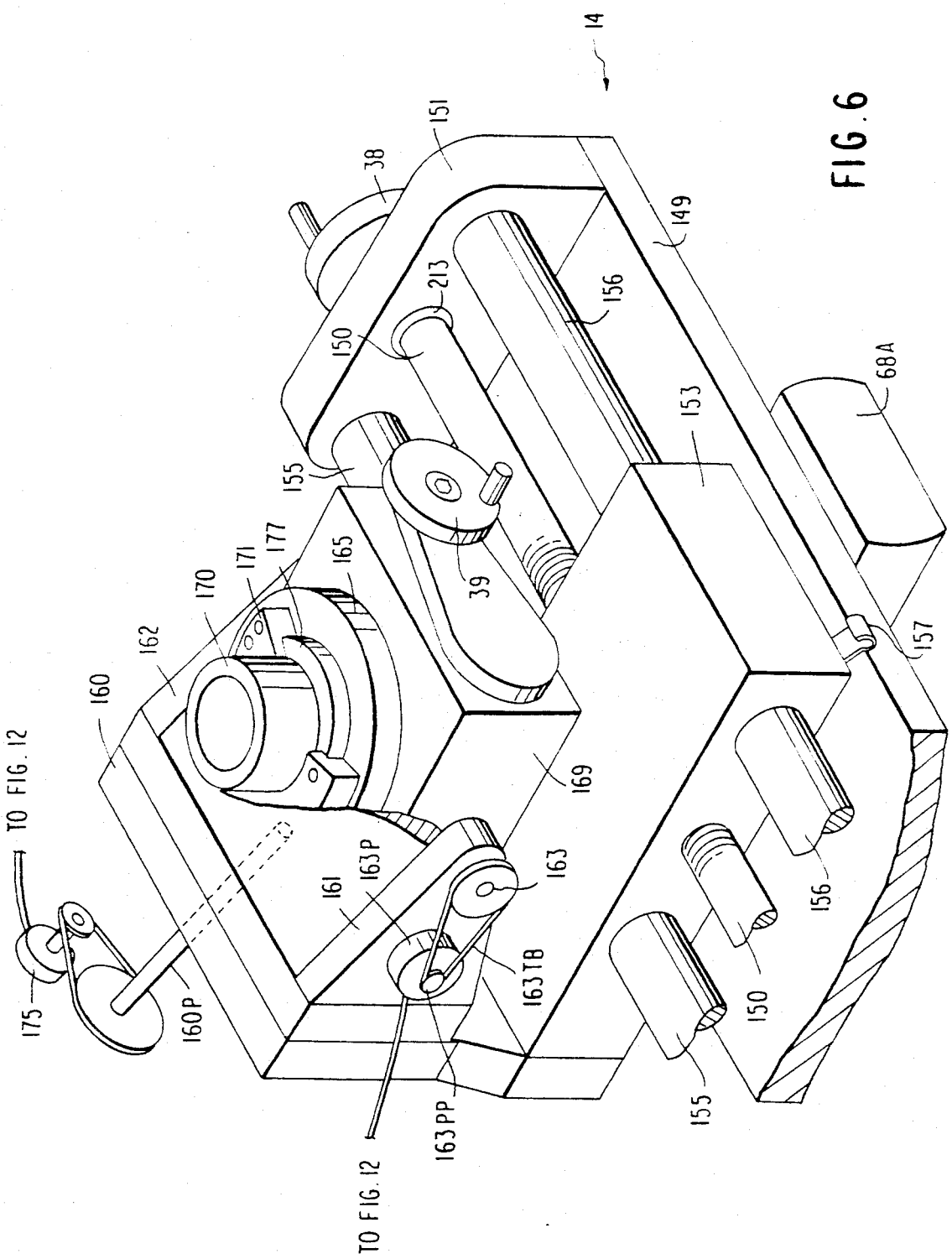
FIG. 6 shows the ankle assembly moving and testing structure.
Figure 7A:
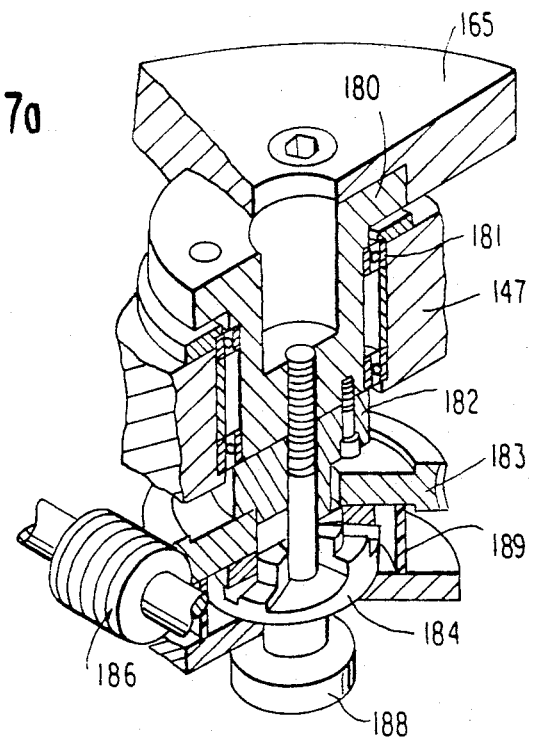
FIGS. 7a, 7b, 7c and 7d show the structure for disengaging the rotation drive to the tibia.
Figure 7B:
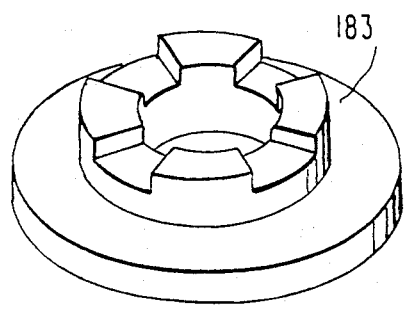
Figure 7C:
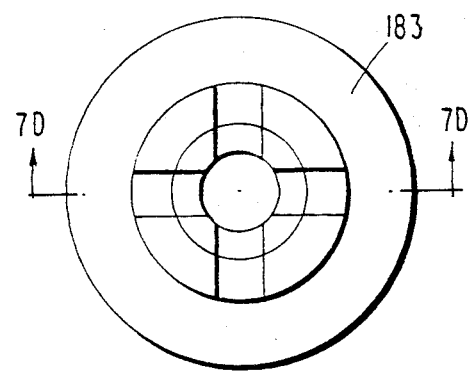
Figure 7D:
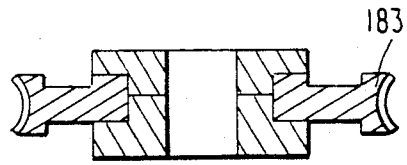
Figure 8:
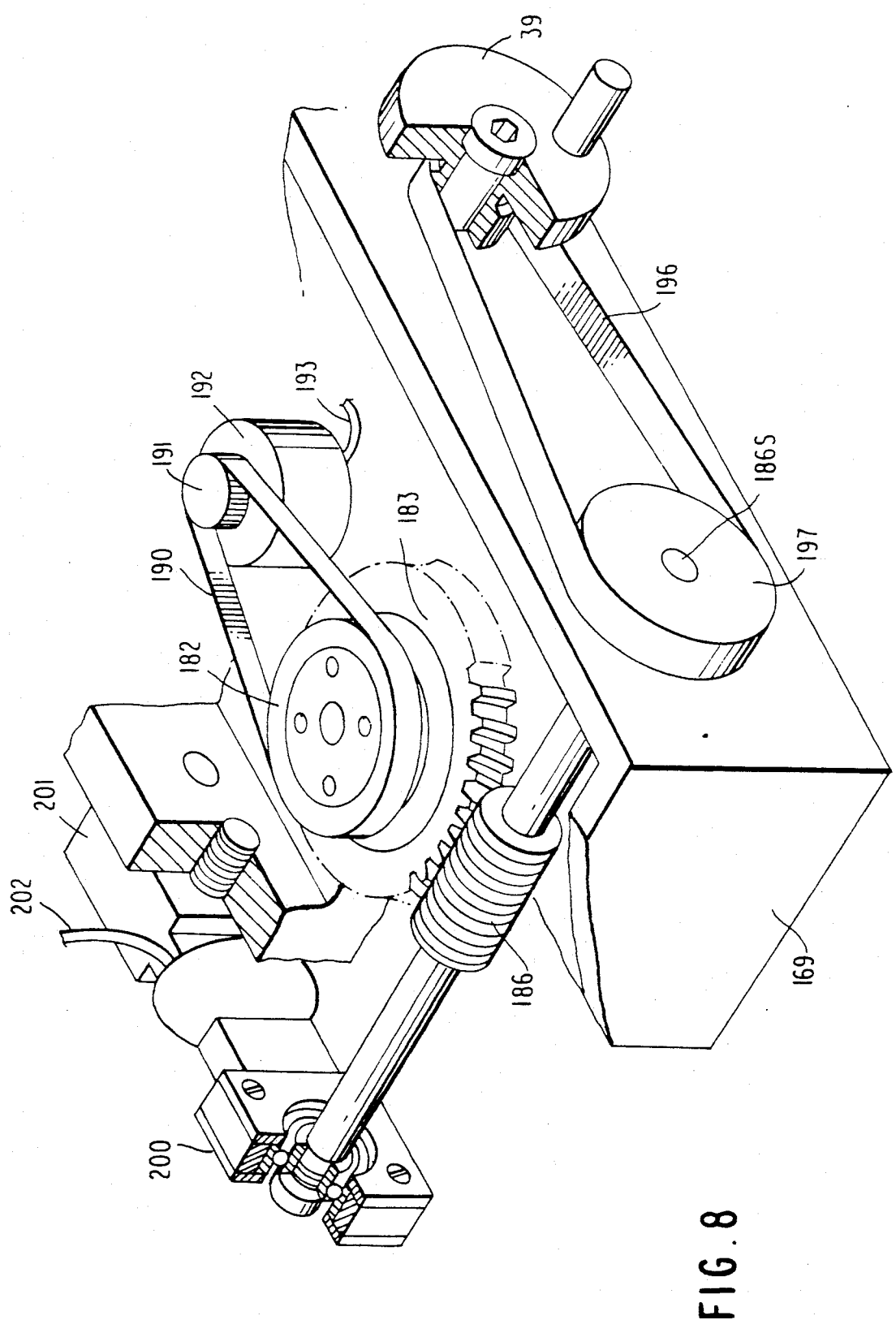
FIG. 8 shows the structure for measuring the angular rotation of the ankle assembly for the transvere plane.

As shown in FIG. 6, the ankle moving or testing structure is mounted on a base plate 149 which, in turn, is bolted to the extension portion 68A of support arm 26 protruding through slot 27 in main frame plate or front panel 21. The ankle input motions, other than, of course, the vertical control by the offset and the body weight control are the varus/valgus angulation controlled by crank handle 38. Thus control 38 rotates lead screw 150 which is journeled for rotation between end brackets 151 and 152 secured in upstanding relation on ankle plate 149. Lead screw 150 is coupled through half nut assembly (to be described more fully hereafter) in carriage 153 which is supported by rollers on a pair of hard (60 case) steel rods 155, 156. A control handle 157 projects outwardly and is used for engaging and disengaging the half nuts which engage and disengage lead screw 150. Control 38 rotates the lead screw 150 which causes the ankle assembly 14 to move in a medial lateral direction. The rotation of the tibia is controlled by control 39 to rotate about a vertical axis or in a so called transverse plane. The carriage 153 supports an upstanding bracket 159 which has yoke 160 pivotally mounted thereon by shaft which permits the ankle 169 to rotate in the coronal plane as the ankle assembly is moved medially or laterally. Bearing pivots 163, 164 in clevis arms 161 and 162 permit the ankle to move in the sagittal plane and a potentiometer 163P is coupled by a timing belt 163TB to bearing pivot 163. The ratios of the diameter of timing belt pulley 163P to potentiometer pulley 163PP is such that small angular movements of pivot pin 163 result in substantially larger rotary movements of potentiometer pulley 163PP. Rotation of control crank 39 again causes the tibia to rotate in the tranverse plane. This is brought about by rotation of tibia or shin bone cup support plate 165 coupled to the control crank 39 by a gearing and disengagement assembly described in greater detail in connection with FIG. 7. The tibia bone 13 (FIG. 1) is mounted in a bone cup 170 with a low melting point alloy or methylmathacryl and held in place by plate 165 by cleats 171 engaging flange 172 of bone cup 170.

The ankle assembly thus moves freely in the medial lateral plane by rolling along steel rods 155, 156 when the half nuts have been moved to release the lead screw 150, the linear bearings engaging rods 155, 156 providing a low friction motion of the ankle back and forth.

As shown in FIG. 7, the structure for disengaging the rotation drive to bone cup 170 and the tibia 13 includes bone cup support plate 165 bolted to a rotating thimble 180 which, in turn, is mounted on precision bearings 181, in ankle assembly block 169, thimble 180 being held in place by coupling member 182 which provides a coupling through the spindle as well as maintaining and preloading the precision bearings 181. A ring gear 183 fits around cup link cap 182. As shown in FIG. 7b (an inverted view), both are grooved in such a manner that they may be caused to be firmly aligned and, in effect, attached by a shift dog 184. Shift dog 184 has an upper surface complementary to the lower surfaces of cap link member 182 and ring gear 183 so that when in its most vertical position provides a solid coupling between cap link 182 and ring gear 183 so that rotation of worm gear 186 causes rotation of ring gear 183 and cup link cap 182 and ultimately the plate 165 and finally, the tibia of the test specimen.

It has been found very desirable to be able to disconnect this drive so that during certain test phases the knee can be permitted to move freely in rotation without any force constraint. To this end, means are provided for disconnecting the drive through 186 and 183 by removing the shift dog 184. This is done by simply rotating control 188 just below the shift dog 184 counter-clockwise to cause the shift dog to drop down approximately ¼ inch thus disengaging the ring gear 183 from cup link cap 182. When the worm gear 183 is not engaged to cup link cap 181 by the shift dog, it is supported by a Teflon ring 189 so that it does not drop down and cause any binding or any frictional interference for the rotation of the system.

Control 39 rotates the tibia. Turning this control causes the ankle to rotate, either "toe in" which is internal or "toe out" which is external rotation. The technique for measuring the rotation of the ankle in the transvere plane is achieved by a sprocket formation on cap 182 which is engaged by a sprocket belt 190 (similar to a timing belt) which is engaged with a sprocket 191 on potentiometer 192, electrical leads coupling the output signal to the electrical circuit shown in FIG. 12. Thus, this provides an electrical signal proportional to ankle rotation. Since the main sprocket 189 is permanently attached to coupling cap 182, even when the drive is decoupled the rotation measurement system is still active. The input force to worm gear 186 through handle crank 39 is indirect by means of timing belt 196 and timing belt sprocket 197 on the end of shaft 186S of worm gear 186. This indirect drive of the worm gear 186 gives an additional advantage since the machine is capable of applying 200 inch pounds of torque to the tibia of a specimen which is twice the amount available from prior machines and the additional mechanical advantages is twice the amount available from prior machines and the additional mechanical advantage is desirable in order to not make it difficult to turn the input control. This provides an overall mechanical advantage of 100 to 1 and it will be appreciated that more or less mechanical advantage may be achieved as desired. The second reason for the timing belt drive input is so that no axial force can be applied to worm gear shaft 186S because this shaft is supported in the axial direction only by the ball bearing and rotation transducer 200. The opposite end 201 of this strain gage transducer 200 is secured to ankle block plate 169. This strain gauge transducer 200 has electrical leads 202 which are coupled to the electrical circuit shown in FIG. 12. Since this transducer 200 accepts all of the axial force in shaft 186S, it can be callibrated in terms of the torque required to drive the tibia since it represents the tangential force on worm gear 186.

While the strain gauge structure is specifically adapted for this apparatus, it will be appreciated that other forms of precision transducers can be designed and constructed all in accordance with the principles of the invention.

Figure 9:
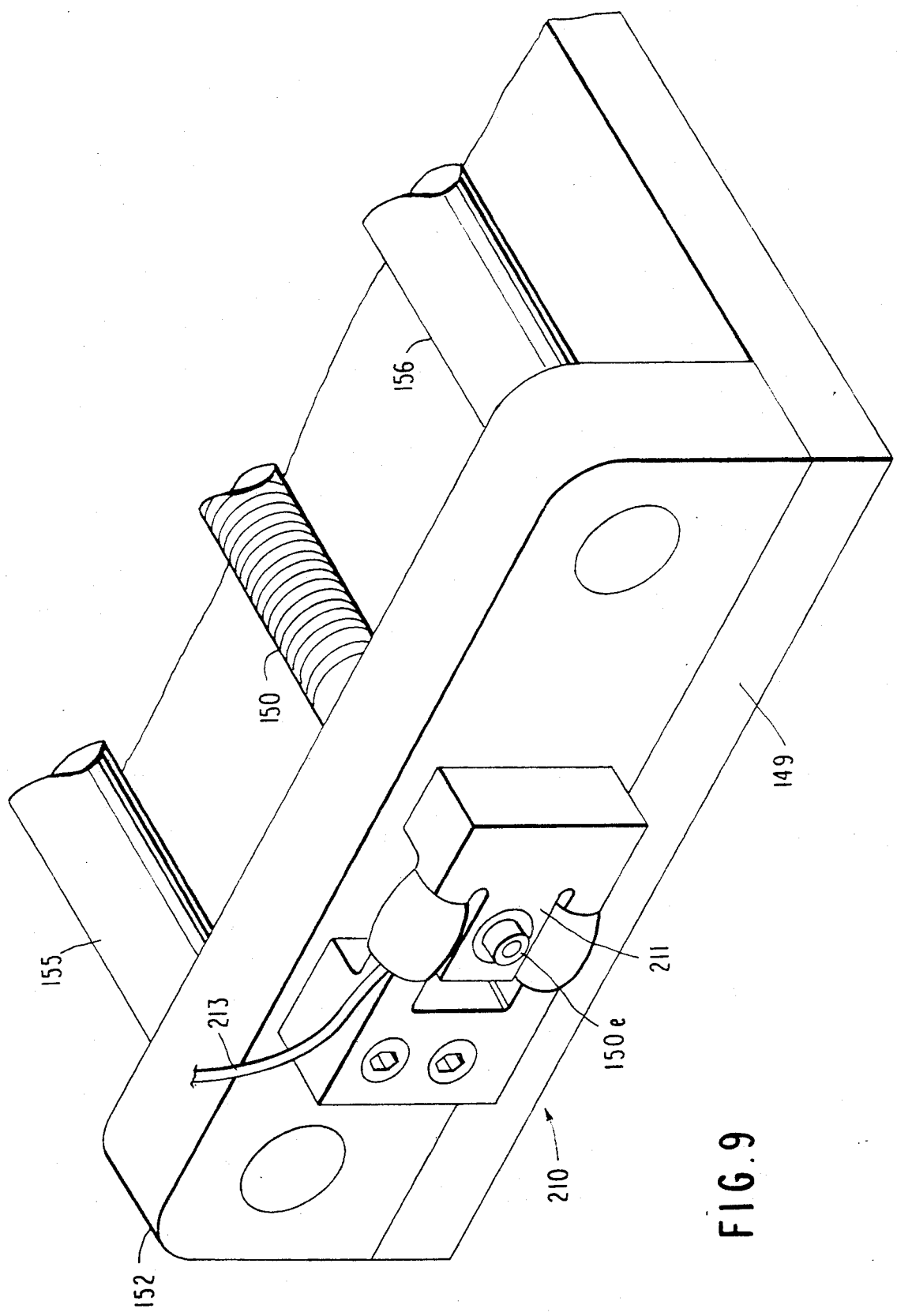
FIG. 9 shows a transducer for the varus/valgus angulation force.

FIG. 9 shows the transducer for the measurement of the varus/valgus angulation force. As described earlier in connection with the transducer 200, this transducer absorbs all of the axial thrust of lead screw 150 and is set so that all of the force from the lead screw is applied to its support bearing 211 and the other end of lead screw 150 is supported in very low friction radial only bearings 213 (see FIG. 6). The axial load on the lead screw 150 in this application as compared to the rotation for the ankle is not as much since this lead screw is normally turned while standing in front of the machine in all of the rotational forces of the handle do not tend to interfer or load the lead screw axially. Electrical leads 213 are used to couple the signals generated in the transducer strain gauges to the electrical circuit shown in FIG. 12. Referring now to FIG. 10, in the base of the ankle assembly block 153 the half nut disconnect assembly is located that decouples the varus/valgus angulation drive (the ankle) so that the ankle assembly 14 can move freely in the medial lateral direction during testing. This, combined with the ability to disconnect the rotational drive provides a means for the ankle assembly 14 to be stabilized by the external forces, that is, body weight in the quadriceps and by the internal geometry of the knee. That is, the geometric structure of the cartilage, the ligaments and the interaction of the tibia and femur.

Connection and disconnection of the varus/valgus angulation is accomplished by moving lever 157. The inner end of control lever 157 is secured to a rotary cam plate 215 which is mounted for rotation in a cut-out in the base of block 153. A pair of cam slots 216 (only one shown in FIG. 10) have changing radius with respect to the center of rotation of the plate and a pair of half nuts 217, 218 have pins 219, 220 in slots 216. The half nuts 217, 218 have threaded half threads 221, 222 which mesh with the threads in lead screw 150 when they are brought together, movement of the lever 157 rotates the cam slots 216 to thereby cam pins 219, 220 and the half nuts 217, 218. If the lever is moved to the right, the half nuts move outward thus releasing the ankle assembly from shaft 150. If the control is moved from the right, the cam slots 216 cause the half nuts 217 and 218 to move inward thus connecting the ankle assemble to the lead screw 150. When the ankle is free to move in the medial/lateral direction, it glides freely on rods 155, 156 and the linear bearing 223, there being four sets of the linear bearings in base block 153 but only one of which is shown in FIG. 10.

The electronic diagram shown in FIG. 12 includes standard components and each of the measurements described hereinabove has the corresponding number of the potentiometer or strain gauge transducer added. Typically, over the angle measurement, the varus/valgus angle potentiometer 175 has about 5 volts imposed upon it and as the wiper arm 175W moves with the varus/valgus angulation motion, the voltage associated with the motion, constitutes the signal which is amplified by an amplifier 175A and adjusted by calibration potentiometer 175C for zero output setting on the varus/valgus angulation is at the true zero so that the system will operate in a plus - minus fashion. The signal output from gain amplifier 175A is applied to a calibration and trim potentiometer 175T and then to an output coupling amplifer 175O. This is then a plus - minus 5 volt maximum signal which is applied to an analog to digital converter 230. The signal going to the meters require different voltage and these are obtained from trim pots, 175TP, for example for the varus/valgus angle pot signal. The signal on wiper 175TPW is applied to a selection switch 231 which couples the output signal to one of the meters on display panel 35. All of the angle measuring potentiometers are set up essentially the ame way with the exception of the hip flexion and ankle flexion potentiometers. Since both the hip and the angles in the sagittal plane must be measured and summed, this is accomplished in amplifiers 235 and 236 so that after the gain and calibration of these two signals in amplifiers 235 and 236, they are applied through calibration potentiometers 235C and 236C to a hip/ankle summing amplifier 237 which provides a total output signal for the knee flexion. The only other exception is the anterior/posterior angle which is a measurement of the tibia when the draw sign test is performed. This is taken off from the ankle flexion potentiometer and amplified at a different level by amplifier 238 and the signal is supplied via calibration potentiometer 238T to an output amplifier 238 and then to the analog and digital converter 230. As shown, the output from the analog to digital converter can be supplied to a computer 240 and the signals can also be applied to a storage unit 241 which may be controlled by computer 240. Amplifier 238 is the only amplifier that has an external zero control and this is because the anterior/posterior transducer is plugged into the front panel jack 36.

The force transducers for the tibia torquie, varus/valgus force, quadriceps force and body weight force are all strain gauge transducer and all use analog devices instrumentation amplifier which provide gain calibration and output drive. The output from these are set again at plus - minus 5 volts but before being applied to the analog digital converter 230. The analog anterior/posterior force transducer is an accessory so that the transducer is not contained within the knee machine itself but the signal and output amplifier is contained and has been present and accepts the output from such a transducer. As shown in FIG. 11, a dual comparator 241 and 242 which receive reference signals from a reference source to set the maximum quadricep force and body weight that can be applied to a given knee. Any time the body weight or quadricep force exceed the maximum values, these comparators provide the relays 245 to be energized so that neither body weight nor off-sets can be increased—they can only be decreased. Additionally, when this occurs, an annuciator 246 is energized to idicate this fact audibly that an overload has occured and it attracts the attention so that the overload can be eliminated.

Figure 11A:
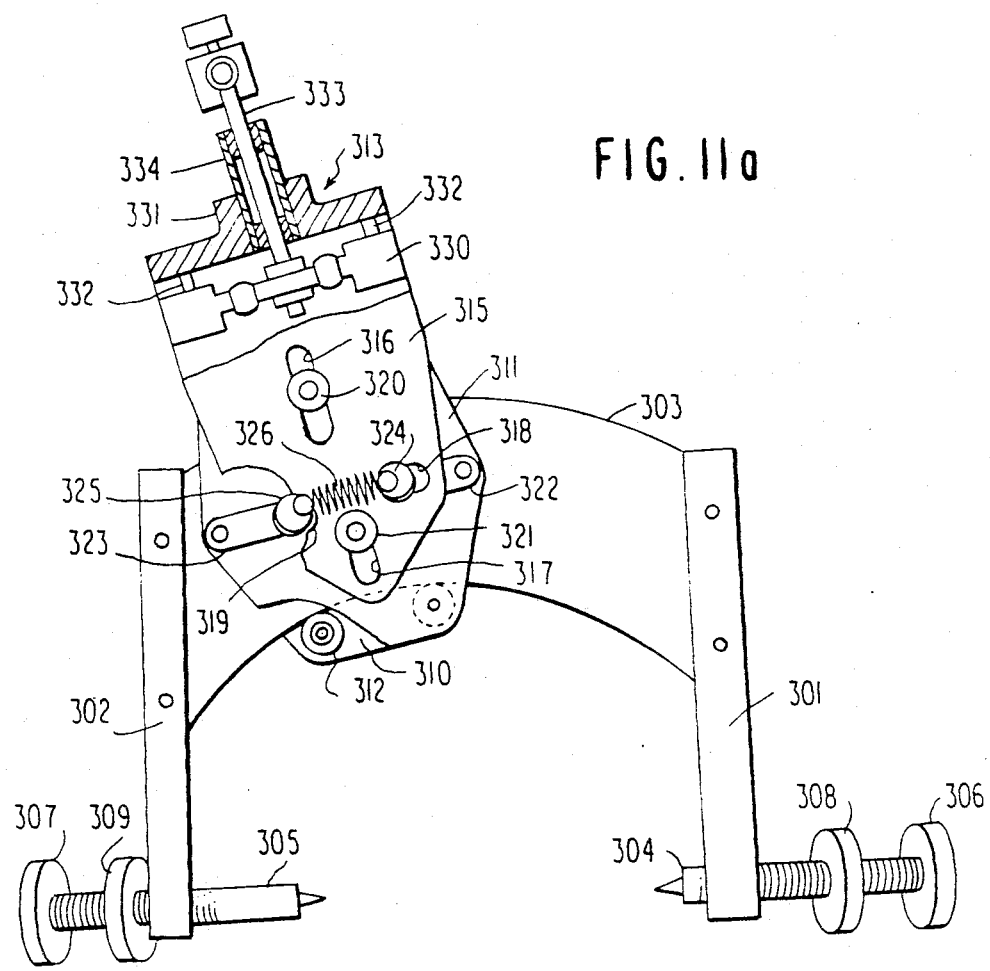
FIG. 11a is a partial isometric view of the anterior/posterior transducer assembly and FIG. 11b shows how the anterior/posterior transducer is used.
Figure 11B:
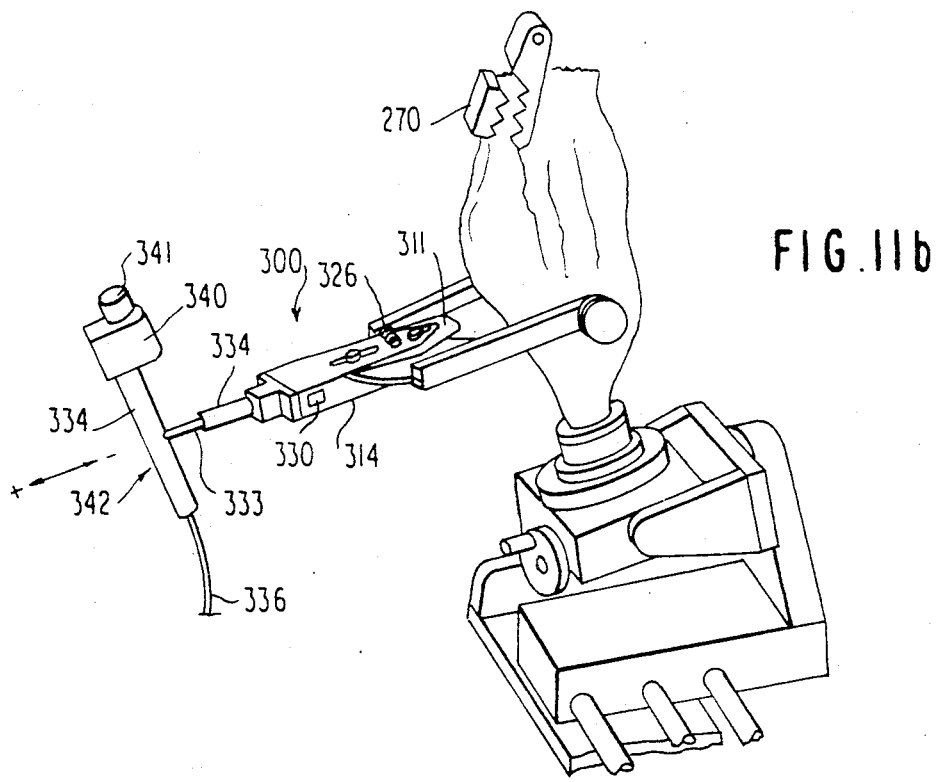

The anterior/posterior force transducer is shown in FIGS. 11a and 11b is mounted on the tibia with pointed screws 280 a few millimeters below the joint line. It may be pushed toward the knee up to about 25 pounds force and pulled away from the knee with up to about 25 pounds force as a test for anterior/posterior stability. The spring and slide mechanism permit this force to be applied over plus or minus about ¾ inch of movement of the slide since the back and forth motion of the tibia on the femur during this test, which is commonly referred to as the drawer sign is only a few millimeters, without the spring and slide assembly, the forces would be applied very abruptly and would be difficult to record. The actual motion of the tibia is measured by the ankle flexion potentiometer.

As shown in FIGS. 11a and 11b, the anterior/posterior transducer assembly 300 includes a pair of spaced arms 301 and 302 connected by arcuate member 303. Such arm has a pointed screw 304, 305 threadably engaged with threaded bores in arms 301 and 302, respectively. Knurled knobs 306 and 307 permit the points of the screws to be driven into the tibia and lock nuts 308 and 309 lock them in position.

The spring and slide assembly includes a pair of plates 310 and 311 which are secured in spaced assembly by four rollers 312, the rollers permitting movement along arcuate member 303. A yoke member 313 has identical arms 314 and 315 which are identically coupled to plates 310 and 311, respectively, so only the coupling to plate 311 need be described. Yoke arm 315 has a pair of longitudinal slots 316 and 317 and a pair of lateral slots 318 and 319. Roller pins 320 and 321 project from plate 311 through slots 316 and 317, respectively. A pair of short pivot arms 322 and 323 the lateral ends of which are pivotally connected to plate 311 and the inner ends of which have roller pins 324 and 325 projecting through slots 318 and 319 and a coil spring 326 is connected between the upper ends of pins 324 and 325, respectively.

The strain gage 330 is spacedly secured to the base 331 of yoke member 313 by spacer screws 332. A hollow shaft 333 passes through the center of strain gage transducer 330 and transmits the push and pull forces described above via transducer 330, spacer screws 332, yoke 313 to the spring slide assembly which then transmits these forces to the knee. Hollow shaft 333 passes through hollow stabilizing tube 334 which is secured to the base 331 of yoke 313 and is rotatably secured to transducer so that no rotary force is applied to the knee during the anterior/poserior measurement. The electrical signal generated in transducer 330 passes is coupled through cable 336 to a male plug which is plugged into jack 36 on the display panel 35, and thence to the electrical circuit shown in FIG. 12. External anterior/posterior zeroing potentiometer 340 having an adjusting knob 341 is secured to handle 342 on the end of rod 334 nd supplied the "external zero" signal on line 343 of FIG. 12.

Figure 13:
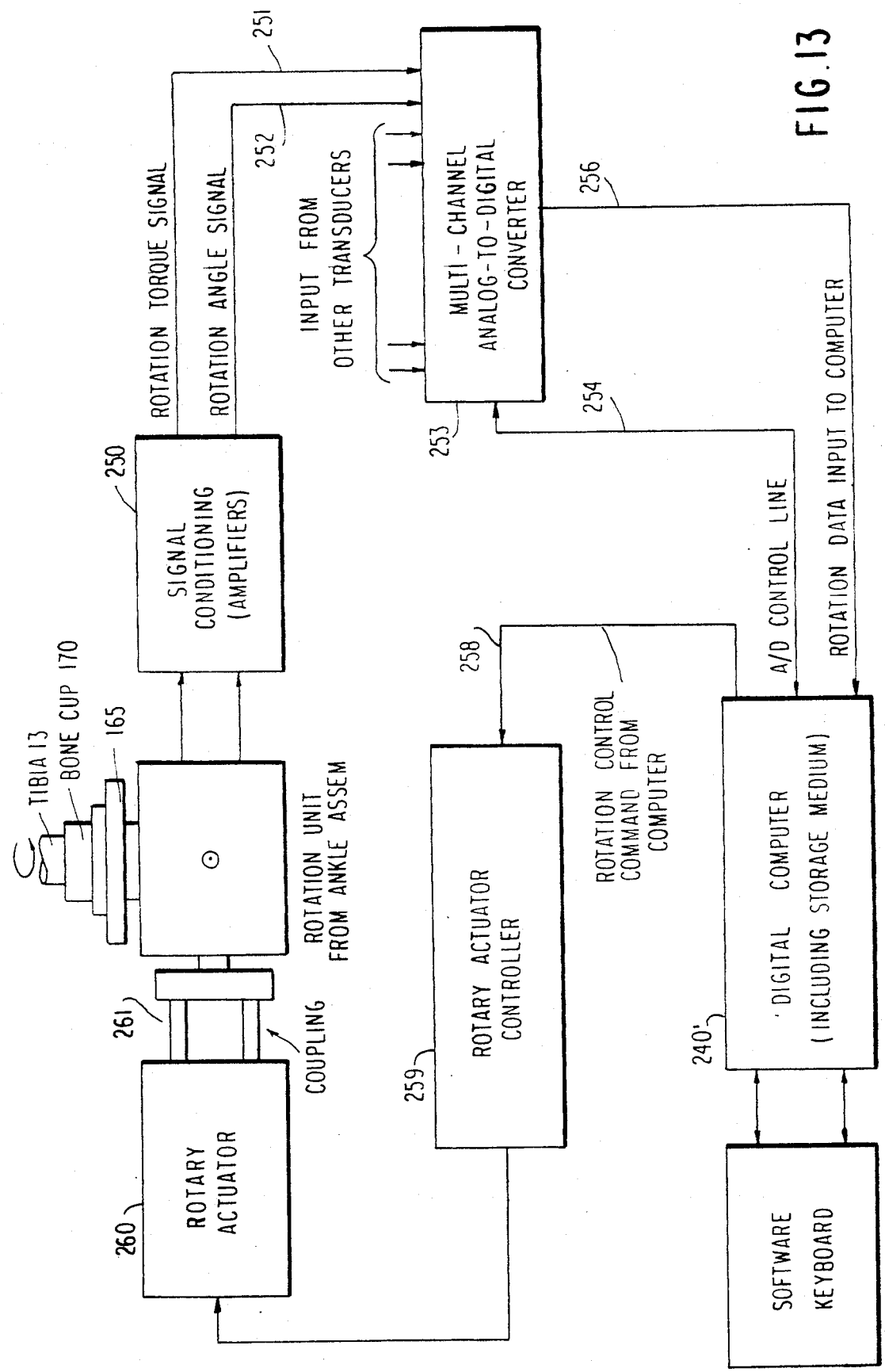
FIG. 13 is a hydraulic circuit block diagram of a servio.

As described earlier herein, each of the controls described earlier herein, can be automated and close loop computer control of each function can be added to the machine, or used in conjunction with the manual controls that have been illustrated. As shown in FIG. 13, the tibia bone 13 is mounted in the ankle bone cup 170 as described earlier herein and the signal from the rotation torque signals and the rotation angle signals are supplied to a conditioning amplifier 250 so that the rotation torque signal on line 251 and the rotation signal on line 252 are applied to a multichannel analog to digital converter 253. As indicated, inputs from other transducers may be applied to the multi-channel analog to digital converter 253 and it will be appreciated that these may be scanned and multiplexed in a conventional manner. A control line 254 from the digital computer 255 provodes synchronism between the operation of the analog digital converter 253 and the output from the analog to digital converter on line 256. As indicated, the rotational data from the ankle unit is being applied to the computer at this particular instant. The computer, under keyboard and software control provides a rotation control command on line 258 which is applied to a rotary actuator controller 259. This signal is then applied to a rotary actuator 260 and a mechanical coupling 261 couples this to the particular ankle unit under control. For a full time closed loop operation, the rotary actuator 260 can be eliminated and the coupling extended over to the rotation unit. And the rotary actuator can be built in to the ankle unit assembly 14. The rotary actuator is a servo motor, a stepper motor or other hydraulic rotary device. The actuator controller is a servo amplifier, a translator or a hydraulic servo control valve that controls the hydraulic pressure from a hydraulic pump. For servo or close loop control, it is not necessary to physically release the rotation in varus/valgus control inputs because the system can be programmed to maintain zero force for either input. Thus the knee could rotate and move medially/laterally as though the drive was disconnected.

It will be appreciated that one of the major features of this invention is that it permits the knee to be stabilized by its own geometry. The machine allows the knee to be tested in all phases for stability before injury, after injury, and after corrective surgery. Moreover, the device records all of the data in real time and stores this for use in a later time which, in contrast to the machines disclosed in the prior art, where only one channel was available at a time and all the other data in real time was lost. Thus, in the prior machines, if it was necessary to plot more than two parameters, the test had to be repeated and if one wanted to do many parameters, the test had to be repeated many times and, of course, during this time the knee was continually deteriorating and there is every reason to believe that the characteristics changed with time so that the data is considered to be invalid if it is tested over and over again and it was difficult to relate the various parameters. The system according to this invention, records all of the data in real time and the investigator can then, at the investigator's convenience, take the data either from the computer's memory and through various easily derived programs chart any parameter against any other parameter in any way desired and at any particular time. Thus, the invention provides an apparatus which is far more flexible than any known prior device. Moreover, it provides a natural test platform for studying the telemechanics and injuries to the knee and provide methods of prevention and it provides an excellent platform for teaching general knee surgery reconstructions, sports medicine, implantation techniques for prosthetic devices. It also permits the study of forces of the bones cement - metal interface of the prosthesis implanted on the knee and cemented in place by polymethacryl material, also known as plexiglass.

The device of the present invention is much easier to use than any other prior art machine and is much safer. Moreover, since the computer can be easily programmed to be "user friendly", it can be programmed so as to lead the researcher through complex tests making it extremely difficult for the researcher not to do things in the proper manner. It is important to note that most of the really important knee data devices of the past and studies have been done without either body weight or quadricep force applied to the knee joint. In fact, the machine disclosed in the article co-authored by the applicant and the present machine are the only known one's that use the quadricep force and body weight both to adjust to the knee. Thus, the present invention provides a multi-function test for knees but it is applicable to multi-function tests of other joints of the human body such as the elbow.

In comparison with prior art machines, which were designed primarily for testing one specific function, and did not generally have quadricep force or body weight and did not have other freedom of motions such as provided by the present invention, the results thereof would be very specific and related only to the test and probably would not relate to a normal knee. As is well known, the knee experiences a slight bit of flexion in various angles, for example when you rotate the tibia, so that it drastically changes the torque versus angulation curves for the tibia.

Furthermore, the present invention is advantageous over the prior art in its ability to perform the drawer sign test. This test is performed by applying a force to the upper extremity of the tibia just below the joint line with a transducer that plugs into the front of the machine. The transducer measures the force which is applied normal to the axis of the tibia posteriorly and anteriorly back and forth. The angularity of the tibia in the anterior/posterior direction is measured by the angle flexion potentiometer. This signal is amplified and off-set set to zero with the external adjustment as described earlier herein which is on the AP anterior/posterior force transducer which gives and accessory. These two things together permit the measurement of the anterior/posterior elasticity of the knee. No other machine can do this with a loaded knee. Attempts in the past to make this measurement (such as disclosed in the Markhoff et al article) does not use any load or quadriceps force.

Since the quadricep force and body weight forces are being applied can be rather extensive and to insure accuracy of the measurement without deflection of component part, the component parts are made much heavier.

While there has been shown and described and illustrated in detail the preferred embodiments of the invention, it will be appreciated that other modifications and embodiments as come within the scope and spirit of the claims appended hereto will become apparent to those skilled in the art and it is intended to encompass such obvious modifications and adaptations within the spirit and scope of the claims appended hereto.

What is claimed is:

1. In a universal knee data machine having femural mounting assembly for the femur bone extending from a knee, tibial mounting assembly for the tibia bone extending from said knee, means for applying a body weight simulating load to said knee, and means for applying a quadriceps force to the knee tendon, the improvement comprising, means connected to said mounting assemblies for simultaneously rotating said femural and tibial mounting assemblies while applying said body weight simulating load and said quadriceps force to said knee.

2. The universal knee data machine defined in claim 1, including means for measuring a plurality of the following selected parameters:

(a) varus/valgus angle
(b) tibial rotation angle
(c) ankle flexion angle
(d) hip flexion angle
(e) tibial torque
(f) varus/valgus force
(g) quadricep force
(h) body weight force.

3. The invention defined in claim 2, including means for measuring and recording all of said parameters substantially simultaneously.

4. The invention defined in claim 3, including computer means coupled to receive and record data on all said parameters.

5. The invention defined in claim 2, including means coupled to receive and record data on the selected parameter.

6. The invention defined in claim 1, including means for permitting said tibial mounting assembly to move freely, means for gradually applying an anterior/posterior force to said knee, means for measuring the anterior/posterior force and means for measuring the anterior/posterior angle when said force has been applied.

7. The invention defined in claim 6, including means carried by said means for applying anterior/posterior force for zero adjusting said anterior/posterior angle measuring means.

8. The invention defined in claim 6, wherein said means for gradually applying an anterior/posterior force includes a spring and slide assembly to prevent sudden application of said anterior/posterior force to said knee.

9. The invention defined in claim 1, including means for releasing said tibial mounting assembly from all angular motion constraints.

10. The invention defined in claim 1, including remote quadricep control means for controlling the amount of quadricep force applied to said knee.

11. The invention defined in claim 10, wherein said remote quadricep control means includes a master force generator, said means for applying a quadricep force to said knee includes a slave force generator, means coupling said master force generator to said slave force generator, and control means coupled to said master force generator to control the force generated thereby.

12. The invention defined in claim 11, wherein said force generators include hydraulic means for operating said force generators.

13. The invention defined in claim 12, wherein said slave force generator is mounted on said femural mounting assembly as a part thereof.

14. The invention defined in claim 13, said slave force generator including an hydraulic cylinder on said mounting assembly, a piston, a piston rod extending from said cylinder, a pulley and cable assembly coupling movement of said piston rod to the knee joint, and a quadricep force transducer between said pulley and cable assembly and said tendon to measure said quadricep force.

15. The invention defined in claim 10, including means for selectively disengaging each said drive means from said femural mounting assembly and said tibial mounting assembly from their respective drives.

16. The invention defined in claim 1, wherein said femural attachment assembly includes a femur attachment cup, and means for locking said femur attachment cup against rotation in the sagittal plane.

17. The invention defined in claim 1, wherein said tibial mounting assembly includes a tibia attachment means, means for rotating said attachment means and means for disabling said means for rotating said attachment means.

18. The invention defined in claim 1, including means for moving said tibial mounting assembly relative to said femural mounting assembly while maintaining load on said knee.

19. The invention defined in claim 1, wherein said tibial mounting assembly includes a carriage mounted for movement along a horizontal axis, drive means for moving said carriage along said axis, and means for selectively engaging or disengaging said drive means with said carriage.

20. The invention defined in claim 1, including means for permitting said tibial mounting assembly to move in a vertical direction in response to change in said quadricep force while maintaining said body weight simulating load constant.

21. The invention defined in claim 1, including a drive means for each said femural mounting assembly, tibial mounting assembly, means for applying a body weight simulating load to said femural and tibial mounting means and said means for applying a quadriceps force to said knee.

22. The invention defined in claim 21, including a hydraulic closed loop control system in at least one of said drive means.

23. The invention defined in claim 1, including means for measuring femural flexion and producing a first signal proportional thereto, means for measuring tibial flexion and producing a second signal proportional thereto, and means for summing said first and second signals.

24. The invention defined in claim 1, including means for limiting the quadricep force applied to said knee to a predetermined quadricep force and means for limiting the body weight simulating load applied to said knee to a selected weight.

25. The invention defined in claim 24, including quadricep control means operable after said predetermined quadricep force has been reached to reduce said quadricep force and body weight control means for reducing said body weight simulting load after said selected weight has been reached.

26. In a method of obtaining data on knee joints wherein the knee joint has a simulated body weight applied thereto while a simulated quadricep pull force is applied to the knee, the improvement wherein constraints on movement of portions of the knee joint and bones therein are selectively removed to obtain data when the knee is stabilized by its own geometry, including the steps of simultaneously measuring and recording data related to a plurality of the following parameters of the knee:
 (a) varus/valgus angle
 (b) tibial rotation angle
 (c) ankle flexion angle
 (d) hip flexion angle
 (e) tibial torque
 (f) varus/valgus torque
 (g) quadricep force
 (h) body weight force, and
 physically modifying the knee structure and then measuring and recording said parameters of the knee.

27. In a method of obtaining data on knee joints wherein the knee joint has a simulated body weight applied thereto while a simulated quadricep pull force is applied to the knee, the improvement wherein constraints on movement of portions of the knee joint and bones therein are selectively removed to obtain data when the knee is stabilized by its own geometry, including the steps of simultaneously measuring and recording data related to a plurality of the following parameters of the knee:
 (a) varus/valgus angle
 (b) tibial rotation angle
 (c) ankle flexion angle
 (d) hip flexion angle
 (e) tibial torque
 (f) varus/valgus torque
 (g) quadricep force
 (h) body weight force, and
 wherein the data is obtained on a normal knee joint and said parameters are measured and recorded, then a non-normal knee is tested in the same way and all said parameters are again measured and recorded and then comparing the recorded data for the normal with the recorded data for the non-normal knee.

28. In a knee data machine for obtaining data on knee joints having a frame, said frame having a first means support a femur bone mounting assembly, a second means supporting a tibia bone mounting assembly and means for applying a force to at least one of said first or second means to simulate a body weight to a knee joint between said femur and tibia bones, and means mounted on said femur bone mounting assembly for applying a tensile force to the knee tendon, the improvement comprising means for selectively removing constraints on movement of portions of said knee joint and bones forming same to obtain data when the knee is stabilized by its own geometry, and means for measuring a plurality of the following parameters:
 (a) varus/valgus angle
 (b) tibial rotation angle
 (c) ankle flexion angle
 (d) hip flexion angle
 (e) tibial torque
 (f) varus/valgus force
 (g) quadricep force
 (h) body weight force
 said means for measuring including means for measuring and recording all said parameters simultaneously.

29. The invention defined in claim 28 including a pair of support arms carried by said frame, one support arm supporting one said assembly, respectively, and means for causing said assemblies to rotate simultaneously about an axis to bring all portions of a knee joint to view from a fixed observation point while said forces are being applied.

30. In a knee loading and testing machine having an ankle mounting assembly and a hip mounting assembly, the improvement comprising means for simultaneously rotating said mounting assemblies about an axis passing through said assemblies.

31. The knee loading machine defined in claim 30 wherein said means for rotating includes a chain and sprocket drive for each said assembly, respectively.

32. The knee loading machine defined in claim 30 including means for applying a tensile force to a knee tendon, the further improvement including a remote control system for controlling the application of said tensile force from a safe and remote location.

33. The knee loading machine defined in claim 32 wherein said remote control system includes a hydraulic servo unit.

* * * * *